(12) United States Patent
Leeflang et al.

(10) Patent No.: US 12,390,095 B2
(45) Date of Patent: Aug. 19, 2025

(54) IMAGING APPARATUS AND SYSTEMS AND METHODS FOR USING THEM

(71) Applicant: CLPH, LLC, Palo Alto, CA (US)

(72) Inventors: Stephen A. Leeflang, Sandy, UT (US); Christian S. Eversull, Palo Alto, CA (US)

(73) Assignee: CLPH, LLC, Palo Alto, CA (US)

( * ) Notice: Subject to any disclaimer, the term of this patent is extended or adjusted under 35 U.S.C. 154(b) by 0 days.

(21) Appl. No.: 16/859,579

(22) Filed: Apr. 27, 2020

(65) Prior Publication Data

US 2020/0329956 A1  Oct. 22, 2020

Related U.S. Application Data

(63) Continuation of application No. 14/692,733, filed on Apr. 21, 2015, now abandoned.

(Continued)

(51) Int. Cl.
| | |
|---|---|
| *A61B 1/05* | (2006.01) |
| *A61B 1/00* | (2006.01) |
| *A61B 1/015* | (2006.01) |
| *A61B 1/018* | (2006.01) |
| *A61B 1/06* | (2006.01) |

(Continued)

(52) U.S. Cl.
CPC ............ *A61B 1/05* (2013.01); *A61B 1/00082* (2013.01); *A61B 1/00177* (2013.01); *A61B 1/00179* (2013.01); *A61B 1/015* (2013.01); *A61B 1/018* (2013.01); *A61B 1/128* (2013.01); *A61B 1/0684* (2013.01); *A61B 2017/00243* (2013.01); *A61B 2017/00349* (2013.01); *A61B 2018/00023* (2013.01); *A61B 2018/00357* (2013.01); *A61B 2018/00363* (2013.01); *A61B 2018/00577* (2013.01); *A61B 2018/00821* (2013.01); *A61B 18/1492* (2013.01); *A61B 2090/064* (2016.02);

(Continued)

(58) Field of Classification Search
CPC ....... A61B 1/00082; A61B 1/05; A61B 1/018; A61B 1/3137; A61B 5/6853; A61B 1/00177; A61B 18/1492; A61B 2017/00243
See application file for complete search history.

(56) References Cited

U.S. PATENT DOCUMENTS

| | | | | |
|---|---|---|---|---|
| 2005/0197623 | A1* | 9/2005 | Leeflang | A61B 1/00078 604/95.04 |
| 2009/0187074 | A1* | 7/2009 | Saadat | A61B 17/0218 600/114 |

(Continued)

*Primary Examiner* — Alexandra L Newton
(74) *Attorney, Agent, or Firm* — William A. English; Vista IP Law Group LLP

(57) ABSTRACT

Systems and methods are provided for injecting one or more agents into tissue within a patient's body that includes a catheter. A needle guide extends from a distal end of the catheter and terminates at a distal tip, e.g., including a foot with an atraumatic contact surface, the needle guide having a cross-section smaller than the distal end and being biased to a curved shape. The needle guide includes a passage communicating from a lumen of the catheter to an outlet at the distal tip, and a needle device is disposed within the passage that may be deployed from the outlet to inject one or more agents into tissue. The catheter also includes an imaging assembly on the distal end configured to acquire images of tissue adjacent the needle guide distal tip.

20 Claims, 10 Drawing Sheets

Related U.S. Application Data

(60) Provisional application No. 62/143,913, filed on Apr. 7, 2015, provisional application No. 62/137,825, filed on Mar. 25, 2015, provisional application No. 62/137,854, filed on Mar. 25, 2015, provisional application No. 62/121,531, filed on Feb. 27, 2015, provisional application No. 61/981,867, filed on Apr. 21, 2014.

(51) Int. Cl.
| | | |
|---|---|---|
| *A61B 1/12* | (2006.01) | |
| *A61B 17/00* | (2006.01) | |
| *A61B 18/00* | (2006.01) | |
| *A61B 18/14* | (2006.01) | |
| *A61B 90/00* | (2016.01) | |
| *A61B 90/30* | (2016.01) | |

(52) U.S. Cl.
CPC .  *A61B 2090/309* (2016.02); *A61B 2090/3614* (2016.02); *A61B 2090/3966* (2016.02)

(56) References Cited

U.S. PATENT DOCUMENTS

| | | | | |
|---|---|---|---|---|
| 2009/0318797 A1* | 12/2009 | Hadani | ................. | A61B 1/018 |
| | | | | 600/424 |
| 2010/0179524 A1* | 7/2010 | Whayne | ............ | A61B 18/1206 |
| | | | | 606/14 |
| 2011/0237940 A1* | 9/2011 | Raleigh | ................ | A61F 2/2433 |
| | | | | 600/425 |
| 2014/0330133 A1* | 11/2014 | Stern | ................... | A61B 5/6853 |
| | | | | 600/509 |

* cited by examiner

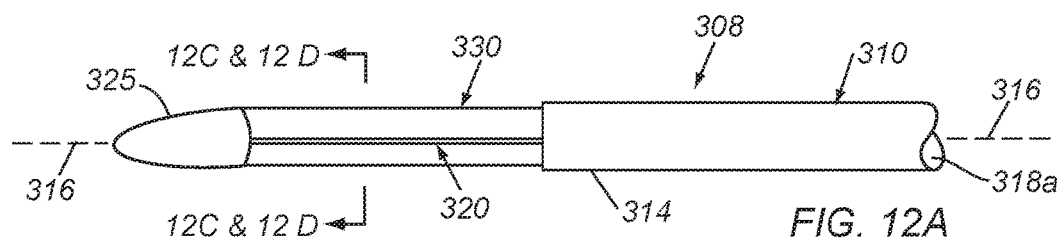
FIG. 12A
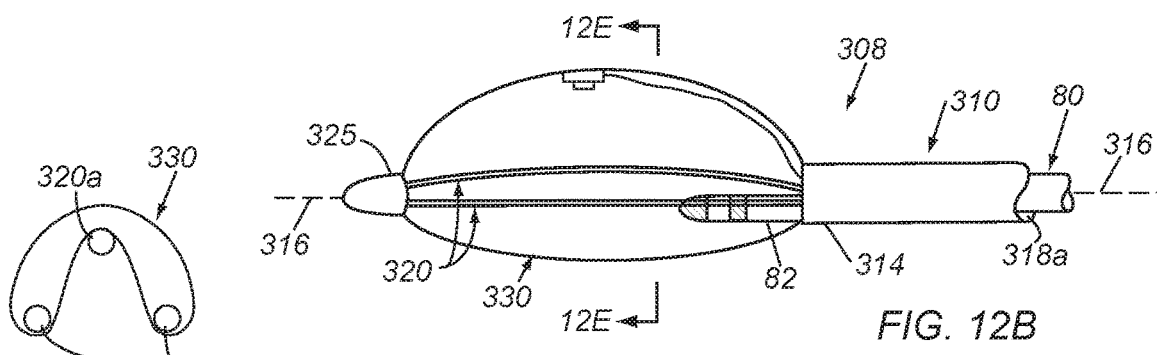
FIG. 12C
FIG. 12B
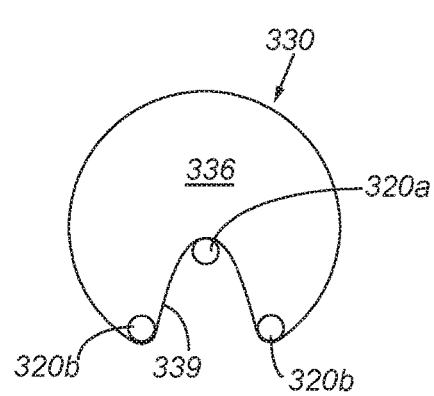
FIG. 12D
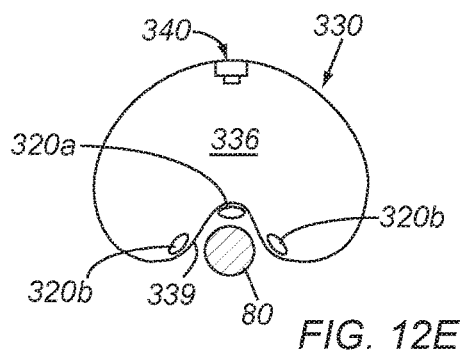
FIG. 12E
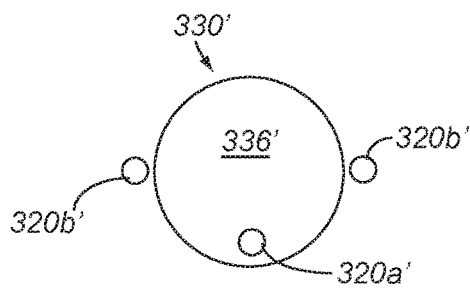
FIG. 13A
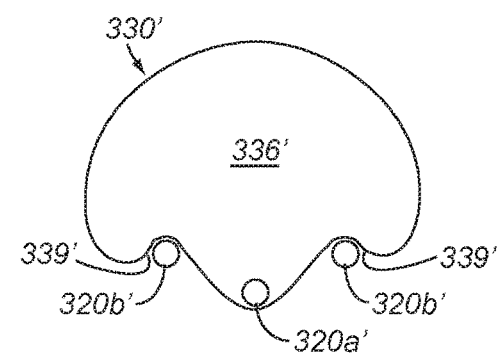
FIG. 13B

IMAGING APPARATUS AND SYSTEMS AND METHODS FOR USING THEM

RELATED APPLICATION DATA

The present application is a continuation of co-pending application Ser. No. 14/692,733, filed Apr. 21, 2015, which claims benefit of provisional applications Ser. Nos. 61/981,867, filed Apr. 21, 2014, 62/121,531, filed Feb. 27, 2015, 62/137,825, filed Mar. 25, 2015, 62/137,854, filed Mar. 25, 2015, and 62/143,913, filed Apr. 7, 2015, the entire disclosures of which are expressly incorporated by reference herein.

FIELD OF THE INVENTION

The present invention relates generally to apparatus, systems, and methods for imaging and/or performing medical procedures, and more particularly to apparatus, systems, and methods for introducing one or more secondary devices into a patient's body, e.g., into the patient's heart, under direct visualization.

BACKGROUND

There are numerous challenges and limitations to current therapies where therapeutic devices are introduced into a range of blood vessels, cavities, and other body lumens. It can be particularly challenging working in the chambers and vessels of the heart as well as the epicardial space immediately surrounding the heart. The number of diagnostic and therapeutic devices for use endocardially and epicardially has grown significantly in recent years. Most of these procedures have at least one challenge in common, namely the difficulty of definitively identifying important anatomical structures and/or delivering or navigating a diagnostic and/or therapeutic device to this precise location, e.g., while avoiding arteries or veins on the surface of the heart, for example, when delivering a cardiac lead or performing ablation. Furthermore, identifying sites of previous treatment or diagnostic procedure (e.g., identifying previously created ablation lesions in order to create additional adjacent lesions) can be challenging.

Therefore, apparatus and methods that facilitate delivering a diagnostic or therapeutic device and/or identifying important anatomical structures and/or sites of previous procedures would be beneficial.

Balloons of various sizes and shapes are used on a wide range of catheter based medical devices for a wide range of purposes. While balloons have been made and disclosed of various shapes, balloons (most especially compliant balloons) have great difficulty taking substantially asymmetric cross-sections orthogonal to the longitudinal axis of the catheter/device given that balloons are generally inclined, via internal pressure, to assume a generally round cross-section when inflated. Providing balloons having asymmetric longitudinal cross-sections may be useful for a variety of medical procedures.

Therefore, apparatus and methods that facilitate imaging and/or delivery of devices during medical procedures would be useful.

SUMMARY

The present invention is directed to apparatus, systems, and methods for performing medical procedures, e.g., within the pericardial space of a patient's body. More particularly, the present invention is directed to apparatus, systems, and methods for introducing one or more secondary devices into a patient's body, e.g., into the patient's heart, under direct visualization.

In accordance with one embodiment, an apparatus is provided for imaging tissue during a medical procedure that includes a tubular member comprising a proximal end, a distal end sized for introduction into a patient's body, a longitudinal axis extending between the proximal and distal ends, and a primary lumen extending from the proximal end to an opening adjacent the distal end; a stabilization member extending distally beyond the distal end to a distal tip, the stabilization member having a cross-section smaller than the distal end; a substantially transparent expandable member comprising a first end attached to the tubular member distal end and a second end attached adjacent the distal tip; and an imaging assembly carried on the stabilization member and oriented to acquire images at least partially transversely relative to the longitudinal axis such that a device deployed from the opening is within a field of view of the imaging assembly.

In accordance with another embodiment, a system is provided for imaging tissue during a medical procedure that includes a tubular member comprising a proximal portion, a distal portion sized for introduction into a patient's body, a longitudinal axis extending between the proximal and distal portions, and a primary lumen extending from the proximal portion to an opening on the distal portion; a stabilization member extending distally beyond the distal portion to a distal tip; a substantially transparent expandable member comprising a first end attached to the distal portion and a second end attached adjacent the distal tip; an imaging assembly carried on the distal portion and oriented to acquire images transversely relative to the longitudinal axis; and a secondary device comprising a distal end sized for introduction through the primary lumen and outlet adjacent the expandable member such the device is within a field of view of the imaging assembly.

In accordance with still another embodiment, a system is provided for imaging tissue during a medical procedure that includes a tubular member comprising a proximal portion, a distal portion sized for introduction into a patient's body, a longitudinal axis extending between the proximal and distal portions, and a primary lumen extending from the proximal portion to an opening on the distal portion; a substantially transparent balloon comprising a proximal end attached to the distal portion distal to the opening and a distal end spaced distally from the distal portion; an imaging assembly carried on the distal portion within an interior of the balloon and oriented to acquire images transversely relative to the longitudinal axis; and a secondary device comprising a distal end sized for introduction through the primary lumen and outlet adjacent the expandable member such the device is within a field of view of the imaging assembly.

In accordance with yet another embodiment, a method is provided for imaging tissue structures within a patient's body that includes introducing a distal end of a tubular member into a body lumen; expanding an expandable member on the distal end within the body lumen; acquiring one or more images of an area adjacent a side wall of the expandable member using an imaging assembly on the tubular member distal end to identify a target location; deploying a device from an opening in the tubular member distal end adjacent the side wall of the expandable member; and positioning the device adjacent the target location while imaging using the imaging assembly.

The apparatus and methods described herein may provide one or more advantages during a medical procedure, such as: 1) providing a stable position for delivering a secondary element or device via an integrated channel/lumen (e.g., an ablation catheter, pacemaker lead, bioptome, injection catheter, needle, and the like); 2) applying desired pressure (e.g., against predetermined anatomy/tissue) against a secondary element or device; 3) substantially isolating a secondary element or device from other components, structures, tissue, and/or anatomy (e.g., thermally, chemically, optically, electrically, and the like); 4) positioning additional design elements relative to the delivery channel (e.g., cameras, sensors, thermocouples, and the like); 5) limiting infused agents or polymers to specific locations; and/or 6) providing cooling or heating in conjunction with desired therapy (e.g., cooling during RF ablation). Additionally, incorporating one or more imaging elements into a balloon may facilitate one or more of 1) anatomical navigation along with or separate from fluoroscopy or other external imaging/mapping modalities (e.g., magnetic, impedance, ultrasound, and the like), e.g., direct visualization may eliminate the need for fluoroscopic guidance during cardiac lead implantation, e.g., making this procedure accessible in areas where capital infrastructure is not available; 2) identification and/or avoidance of sensitive anatomy (e.g., arteries, veins, pacing nodes, nerves, surrounding tissues, such as the esophagus, lungs, and the like); 3) substantial alignment of secondary devices relative to an imaging field and visualization of secondary device and proximate anatomy; 4) visualization of a therapy delivery application site (e.g., visualization of an ablation lesion, application of biologic treatments, and the like); and/or 5) evaluation of delivered therapy (e.g., quality of lesion, position of lesion relative to anatomy or other lesions, and the like). Additionally, positioning the main delivery lumen in close proximity to the main shaft wall and terminating the exit proximal to the balloon (e.g., not passing the secondary device through the balloon), may facilitate the ability to "slit out" any device to be left in after removal of the imaging/delivery device (e.g., pacemaker leads, drains, and the like).

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 12A and 12B are side views of an exemplary embodiment of a catheter including a balloon expandable to an asymmetrical shape in collapsed and expanded conditions, respectively.

FIGS. 12C and 12D are cross-sectional views of the catheter of FIGS. 12A and 12B, taken along slice 12C&12D-12C&12D in FIG. 12A, showing the balloon in collapsed and expanded configurations, respectively.

FIG. 12E is a cross-sectional view of the catheter of FIGS. 12A and 12B, taken along slice 12E-12E in FIG. 12B.

FIGS. 13A and 13B are cross-sectional views of an alternative embodiment of a balloon in collapsed and expanded configurations, respectively.

DETAILED DESCRIPTION OF THE EXEMPLARY EMBODIMENTS

Figure 1:
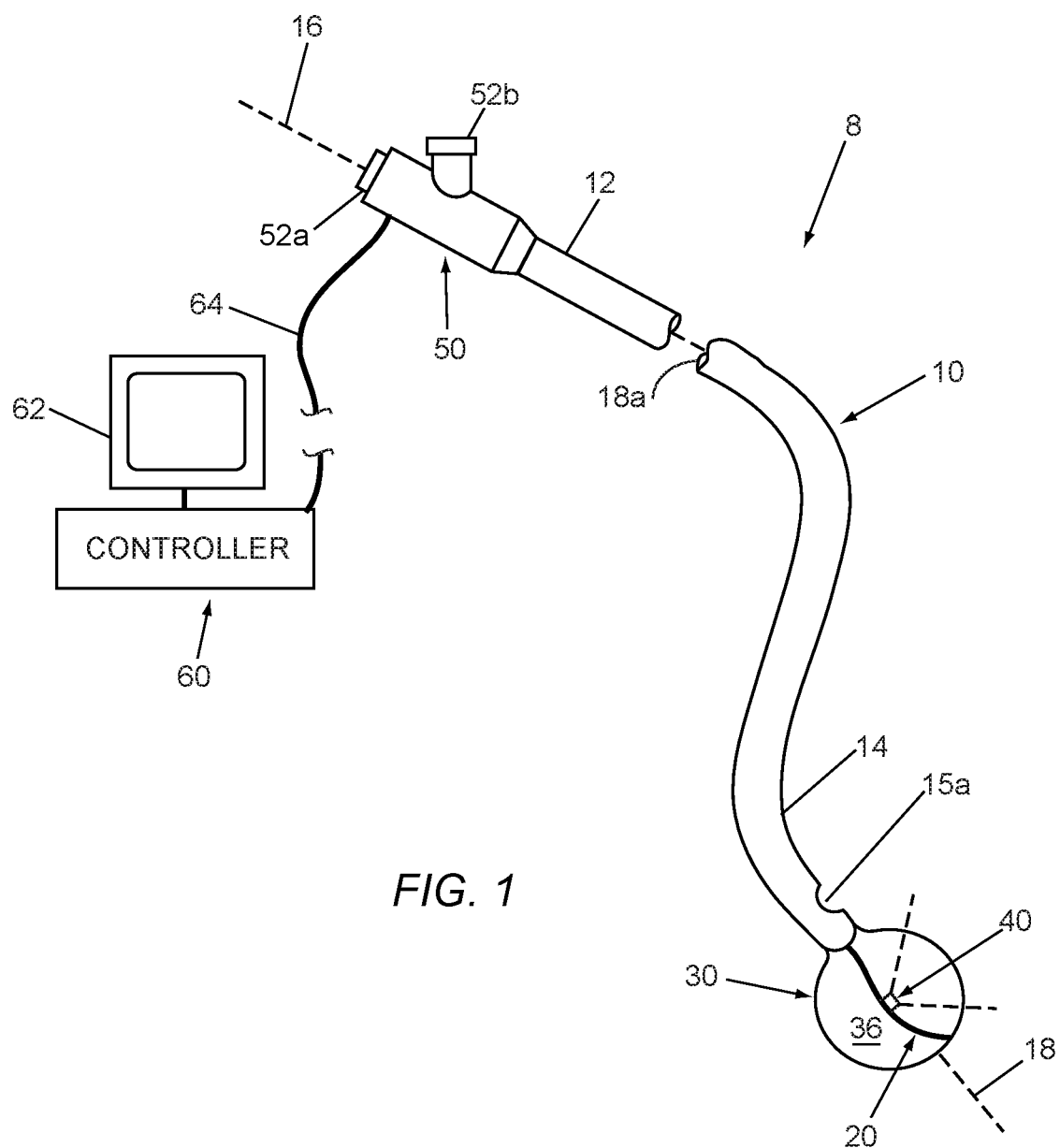
FIG. 1 is a perspective view of an exemplary embodiment of an imaging apparatus.

Turning to the drawings, FIG. 1 shows an exemplary embodiment of an apparatus 8 for performing a medical procedure within a patient's body, e.g., for imaging within the patient's body and/or introducing one or more devices into the patient's body. In exemplary embodiments, the apparatus 8 may be part of a system including one or more additional devices, e.g., a pacemaking or other cardiac lead 70, an ablation catheter or probe 80 (not shown, see, e.g., FIGS. 4A-5B), a needle or other injection device (not shown), and the like. Optionally, the system may include one or more additional components or devices, e.g., an access or delivery sheath, one or more stylets, and/or one or more guidewires or rails (all not shown), to facilitate introduction and/or use of the apparatus 8.

As shown, the apparatus 8 generally includes a catheter or other elongate member 10 including an elongate stabilization member 20 carrying a balloon 30 and an imaging assembly 40. The catheter 10 is an elongate tubular member including a proximal portion or end 12 carrying a handle or hub 50, a distal portion or end 14 sized for insertion into a patient's body and carrying the stabilization member 20, a central longitudinal axis 16 extending between the proximal and distal ends 12, 14, and one or more lumens 18 extending between the proximal and distal ends 12, 14.

Figure 2A:
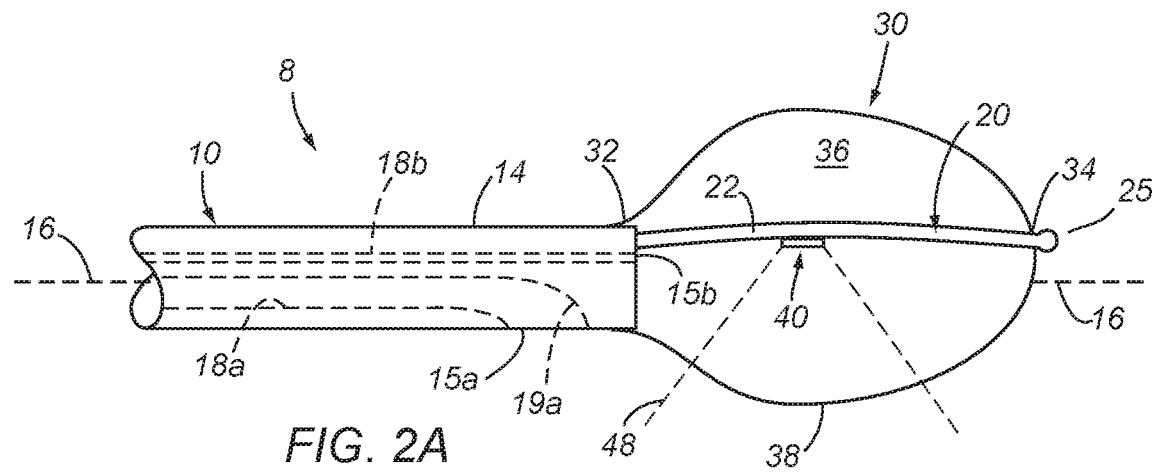
FIGS. 2A and 2B are side and top views, respectively, of a distal portion of an exemplary embodiment of the imaging apparatus of FIG. 1 including a lateral imaging assembly carried within a balloon adjacent a primary lumen opening in a side wall of the distal portion.

For example, the catheter 10 may include a primary or device lumen 18a extending from a port 52a on the handle 50 to an opening or side port 15a in the distal portion 14 adjacent the balloon 30. In addition, as shown in FIG. 2A, the catheter 10 may include an inflation lumen 18b, e.g., extending from a side port 52b on the handle 50 to an outlet 15b on the distal portion 14, that communicates within an interior 36 of the balloon 30, e.g. to deliver inflation media into the interior 36 to expand the balloon 30 and/or aspirate inflation media to collapse the balloon 30, as described further elsewhere herein.

In addition or alternatively, the catheter 10 may include one or more additional lumens extending at least partially between the proximal and distal ends 12, 14. For example, one or more imaging lumens may be provided for receiving one or more electrical cables, fiberoptic elements, and the like (not shown) coupled to the imaging assembly 40, e.g., for providing power to the imaging assembly 40 and/or for providing images output from the imaging assembly 40, as described elsewhere herein. Optionally, one or more steering lumens may be provided for receiving a steering cable or pull wire and/or stylets (also not shown), e.g., for deflecting, bending, or otherwise manipulating the distal portion 14 during delivery and/or use. In addition, one or more infusion or aspiration lumens (not shown) may be provided for delivering fluids into a region adjacent the distal portion 14 and/or aspirating fluid from the region, e.g., for cooling and/or heating elements on or adjacent the distal portion 14, for delivering one or more diagnostic or therapeutic agents into a region adjacent the distal portion 14, and the like.

In one embodiment, a proximal section of the catheter 10 may include a relatively large central lumen and one or more components may extend through the central lumen, e.g., within separate tubular bodies to at least partially isolate them from one another. Optionally, within a distal section of the catheter 10 adjacent the distal portion 14, the configuration of the lumens 18 may change to provide different mechanical properties and/or other characteristics for the distal section, e.g., providing separate lumens molded or otherwise formed in the distal portion 14.

Optionally, the distal portion 14 may include one or more features to enhance visibility under fluoroscopy, ultrasound, Mill or other imaging modalities, e.g., by providing one or more radiopaque markers on and/or doping one or more regions of the distal portion 14, the stabilization member 20, and/or the balloon 30, e.g. as known in the art. In addition or alternatively, electrodes may be incorporated into the apparatus 8, e.g., for electrical sensing and/or impedance based navigation (not shown). Likewise, other sensors, e.g., pressure sensors, may be incorporated into the apparatus 8 to aid in navigation within the body.

The catheter 10 may be substantially flexible, semi-rigid, and/or rigid along its length, and may be formed from a variety of materials, including plastic, metal, and/or composite materials, as is well known to those skilled in the art. For example, the catheter 10 may be substantially flexible at the distal portion 14 to facilitate advancement through tortuous anatomy, and/or may be semi-rigid or rigid at the proximal portion 12 to enhance pushability and/or torqueability of the catheter 10 without substantial risk of buckling or kinking.

In an exemplary embodiment, the catheter 10 may include an inner liner, e.g., at least partially or entirely surrounding or otherwise defining the primary lumen 18a, a reinforcement layer surrounding the inner liner, and an outer jacket surrounding the reinforcement layer (not shown), each of which may extend at least partially between the proximal and distal ends 12, 14 of the catheter 10. The reinforcement layer and/or outer jacket may be attached to the inner liner, e.g., by laminating, adhering, adhesive bonding, ultrasonic welding, reflowing or other heating, and the like. In an exemplary embodiment, the primary lumen 18a and/or one or more of the additional lumens may include lubricious material or may be formed from one or more layers of thermoplastic or other polymeric material including one or more coatings on the inner surface having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein. In an exemplary embodiment, the outer jacket may be formed from PEBAX, nylon, urethane, and/or other thermoplastic material, e.g., such that the material of the outer jacket may be heated and reflowed and/or otherwise formed around the components.

The handle or hub 50 may be provided on the proximal end 12 of the catheter 10, e.g., configured and/or sized for holding and/or manipulating the apparatus 10 from the proximal end 12 and/or including one or more ports 52 communicating with respective lumens within the catheter 10. For example, as described previously, the port 52a may communicate with the primary lumen 18a and may include one or more seals (not shown) to provide a substantially fluid-tight seal while accommodating inserting one or more devices into the port 52a and primary lumen 18a. Side port 52b may communicate with the inflation lumen 18b, e.g., for delivering fluid into and/or aspirating fluid from the interior 36 of the balloon 30, as described elsewhere herein. For example, a syringe or other source of inflation media (not shown) may be coupled to the side port 52b for introducing and/or removing fluid, e.g., saline, nitrogen, air, and the like, into and/or from the interior 36 of the balloon 30.

The handle 50 and/or proximal end 12 may also include one or more connectors, e.g., electrical connectors, and the like (not shown), for connecting the imaging assembly 40 to a controller 60, e.g., including a power source, processor, display 62, and the like, via one or more cables 64. Optionally, if the catheter 10 includes one or more steering elements, corresponding actuators, e.g., sliders or rotary knobs (not shown) may be provided on the handle 50 for actuating the steering elements, e.g., to deflect and/or straighten the distal portion 14.

Figure 2B:
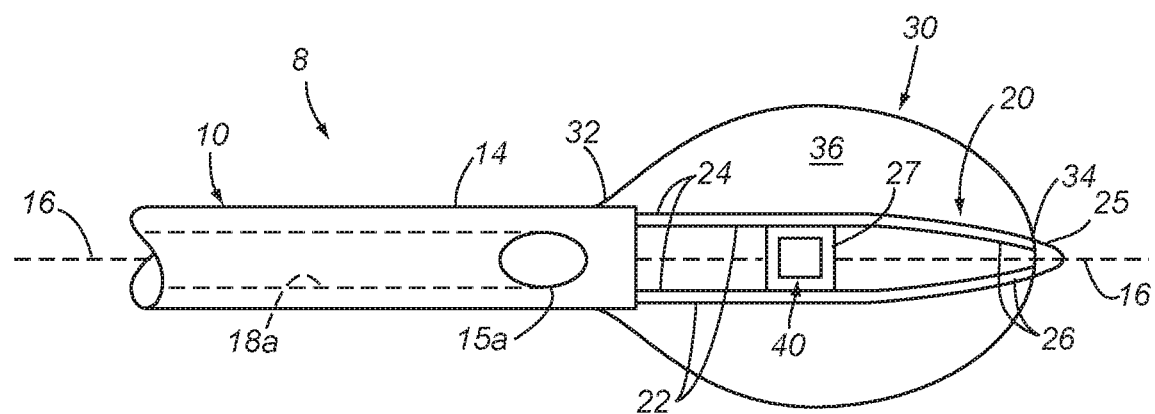

Turning to FIGS. 2A and 2B, an exemplary embodiment of the distal portion 14 of the catheter 10 is shown, providing additional detail of the components carried thereon. For example, as shown, the stabilization member 20 extends from the distal end 14, e.g., generally along the longitudinal axis 16 and terminates at a distal tip 25, which may be rounded, bulbous, and/or otherwise substantially atraumatic to facilitate advancement and/or other manipulation without substantial risk of damaging tissue contacted by the distal tip 25.

In the embodiment shown, the stabilization member 20 is a loop including first and second arms 22 extending between first ends 24 coupled to the distal end 14 of the catheter 10 and second ends 26 coupled together at the distal tip 25. The arms 22 may extend substantially parallel to the longitudinal axis 16 such that the arms 22 generally define a plane offset from the longitudinal axis 16. Alternatively, the arms 22 may have a curvilinear shape, e.g., including an intermediate region that curves away from the longitudinal axis 16 further than the first and second ends 24, 26, as described elsewhere herein. In another alternative, the stabilization member 20 may include a single elongate member, e.g., a hollow tube or solid wire (not shown) extending to the distal tip 25. Optionally, in this alternative, the stabilization member 20 may include a lumen, e.g., for delivering one or more fluids distally beyond the balloon 30 and/or a steering lumen having a steering element therein for bending or otherwise modifying the shape of the stabilization member 20, e.g., to adjust a field of view of the imaging assembly 40, as described elsewhere herein.

In an exemplary embodiment, the stabilization member 20 may be formed from a single section of wire shaped to define the arms 22 and the rounded distal tip 25. Alternatively, the stabilization member 20 may be formed from one or more wires, one or more tubes, and/or from a sheet of material, e.g., having sections removed, for example, by laser-cutting, etching, stamping, machining, and the like, to provide the arms 22. The resulting stabilization member 20 may be heat-treated or otherwise shaped and/or biased to a substantially flat or curvilinear shape and yet may be sufficiently flexible to bend and/or be directed to a substantially straightened and/or other compressed shape (not shown), e.g., to facilitate introduction into a patient's body, as described elsewhere herein. For example, the stabilization member 20 may be formed from elastic material, such as Nitinol, plastic, and the like, that may support the balloon 30 and/or imaging assembly 40, yet may deflect as desired during introduction and/or other manipulation.

As best seen in FIG. 2B, the stabilization member 22 carries the imaging assembly 40, e.g., at an intermediate location between the first and second ends 24, 26, for example, generally centered within the interior 36 of the balloon 30. Alternatively, the imaging assembly 40 may be carried at other locations on the distal portion 14, e.g., on the balloon wall and/or a separate support structure (not shown), e.g., similar to other embodiments herein. In an exemplary embodiment, one or more cross-members or other support structure 27 may extend between the arms 22 to provide a substantially flat surface for receiving the components of the imaging assembly 40. Alternatively, the imaging assembly 40 may be contained within a housing and mounted directly between the arms 22 at the desired location.

With continued reference to FIGS. 2A and 2B, the balloon 30 may include a proximal end 32 attached to the distal end 14 of the catheter 10 and a distal end 34 attached adjacent the distal tip 25 of the stabilization member 20. In exemplary embodiments, the proximal end 32 of the balloon 30 may be secured to the outer surface of the catheter 10, e.g., using an adhesive, heating, sonic welding, an interference fit, an outer collar (not shown), and the like. Similarly, the distal end 34 of the balloon 30 may be attached to the second ends 26 of the arms 22 and/or over the distal tip 25, e.g., using an adhesive, heating, sonic welding, and the like.

The balloon 30 may be expandable from a contracted or delivery condition (not shown) to an enlarged condition when fluid is introduced into an interior 36 of the balloon 30, e.g., as shown in FIGS. 1, 2A, and 2B. Optionally, the balloon 30 may be shaped such that, in the enlarged condition, the balloon 30 may define an asymmetrical shape, e.g., to provide a guide channel for a device introduced through the catheter 10, to enhance a field of view of the imaging assembly 40, and the like, as described elsewhere herein.

In an exemplary embodiment, the balloon 30 may be formed from compliant and/or elastic materials, e.g., elastomeric materials such as silicone, latex, isoprene, and chronoprene. The compliance of the balloon 30 may facilitate clearing fluid between the surfaces, e.g., the side wall 38 of the balloon 30, to facilitate imaging, as described elsewhere herein. Alternatively, the balloon 30 may be formed from substantially noncompliant material, e.g., polytetrafluoroethylene (PTFE), expanded polytetrafluoroethylene (EPTFE), fluorinated ethylenepropylene (FEP), polyethylene teraphathalate (PET), urethane, olefins, and polyethylene (PE), such that the balloon 30 expands to a predetermined shape when fully inflated to the enlarged configuration. The material may be sufficiently flexible and/or elastic such that the side wall 38 may conform substantially to the shape of contacted tissue structures, e.g., the endocardium and/or epicardium of a patient's heart, which may displace blood or other fluid from between the side wall 38 and the contacted tissue to facilitate imaging through the balloon 30. Further, the conforming balloon, when filled with radiopaque material and viewed under fluoroscopy, may highlight anatomy to which it has conformed. Additionally, the balloon 30 provides an atraumatic surface, e.g., which may be used to safely navigate within the body, separate tissue planes or adhesions, cross valves, probe tissues, and the like The material may also be substantially transparent, i.e., allow light from the imaging assembly 40 to pass therethrough and/or be reflected off tissue or other structures beyond the side wall 38 of the balloon 30 back to the imaging assembly 40, as described elsewhere herein. Exemplary transparent materials include silicone, PET, natural urethane, and some nylons. As used herein, "transparent" refers to any material and/or fluid that may permit sufficient light to pass therethrough in order to identify or otherwise visualize objects through the material and/or fluid. "Light" as used herein may refer to one or more ranges of light radiation within the visible spectrum, but may also include other spectra, such as infrared ("IR") or ultraviolet ("UV") light.

The imaging assembly 40 generally includes one or more cameras or other imaging elements and one or more light sources (not shown), e.g., mounted on the support structure 27 or directly to the arms 22. As a result, the field of view 48 of the imaging assembly 40 may extend transversely relative to the longitudinal axis 16 of the catheter 10. For example, a center axis of the field of view 48 may be substantially perpendicular to the longitudinal axis 16 of the catheter or may define an acute angle relative to the longitudinal axis 16. With the plane defined by the arms 22 of the stabilization member 20 offset from the longitudinal axis 16, the field of view 48 may be oriented across the longitudinal axis 16 towards the side wall 38 and/or towards the opening 15a of the primary lumen 18a, which may maximize the size of the field of view 48 beyond the side wall 38, e.g., such that any devices advanced from the opening 15a may enter the field of view 48 and be imaged, as described further elsewhere herein. Further, with the arms 22 spaced apart from one another on either side of the field of view 48, the stabilization member 20 may remain outside the field of view 48 when images are acquired using the imaging assembly 40.

In an exemplary embodiment, the imaging assembly 40 may include one or more CMOS (complementary metal-oxide-semiconductor) or CCD (charge-coupled device) sensors that are exposed within the interior 36 of the balloon 30 for capturing light images through the balloon 30. Alternatively, the imaging assembly 40 may include a bundle of optical fibers, e.g. a coherent image bundle, that extends between the proximal and distal ends 12, 14 of the catheter 10 and terminates at the support structure 27 to orient the ends of the fibers transversely.

Optionally, one or more lenses, filters, prisms, mirrors, and the like (not shown) may be coupled to and/or used in conjunction with the imaging sensor(s) and/or fiber ends, e.g., to focus light from beyond the side wall 38 of the balloon 30 onto the active area of the imaging assembly 40, direct the field of view 48 of the imaging assembly 40, and/or filter undesired wavelengths of light, as known to those skilled in the art. Optionally, the imaging assembly 40 may be covered with a transparent protective coating, e.g., to prevent inflation media within the interior 36 from contacting components of the imaging assembly 40.

The one or more light sources may include one or more LEDs (light emitting diodes) and/or other light sources mounted on the support structure 27 and/or arms 22 adjacent the sensor(s) and/or imaging fiber ends, e.g., to deliver light into the interior 36 and/or through the side wall 38 of the balloon 30. Alternatively, one or more optical fibers (not shown) may be provided that extend from the proximal end 12 of the catheter 10 to the support structure 27, e.g., as part of an imaging fiber bundle, to emit light from a source in the controller 60 (shown in FIG. 1). The one or more light sources may be positioned at predetermined locations within the balloon 30, e.g., on the stabilization member 20 and/or the balloon wall, to increase uniformity and/or intensity of illumination, and/or to separate heat generated by a light source from other device components, e.g., cameras and the like, and/or from areas of the balloon 30 that may contact heat sensitive structures in the body. The inflation media within the interior 36 may provide a heat sink, e.g., to dissipate any heat generated during operation by the light sources and/or other chips or components mounted on the support structure 27 and/or otherwise included in the imaging assembly 40. Optionally, fluid may be circulated into and out of the interior 36, e.g., to further dissipate heat, if desired.

In an exemplary embodiment, the light sources may include a plurality of LEDs that emit visible white light and a plurality of LEDs that emit visible red light. Including additional light sources other than white may increase the bandwidth of light received by the imaging assembly 40 (for example, red light may make red tissues appear more natural in images). In addition or alternatively, the light sources may be doped to increase the bandwidth emitted. Optionally, other sources of non-visible light, e.g., emitting infrared or ultraviolet light may be included, e.g., emitting longer wavelengths that may allow deeper penetration into tissue, e.g., to identify vessels below the tissue contact surface, such as vessels within the myocardium of a heart, and/or to assess depth of ablation lesions created.

A controller 60 (e.g., as shown in FIG. 1) may provide a power source for the imaging assembly 40, e.g., to operate the sensor(s) and/or light sources, and/or may receive image data from the sensor(s), e.g., via cables (not shown) within the catheter 10 and an external cable extending from the handle 50 to the controller (also not shown). In addition, the controller 60 may include a display 62, one or more processors, memory, and the like (not shown) to process, display, and/or store the images acquired from the imaging assembly 40. For example, the imaging element may acquire digital images and may convert the image data onboard to analog signals, which may be conveyed via the cables 64 to the controller 60, which may convert the images back to digital images and/or further process the images for display 62. Alternatively or in addition, one or more features of the controller 60 may be incorporated into the handle 50 of the apparatus 8, even to the extent that all functionality of a controller is so incorporated. Additional information on imaging assemblies and/or balloons that may be provided on the catheter 10 are disclosed in U.S. Pat. No. 6,979,290, the entire disclosure of which is expressly incorporated by reference herein.

In addition, as best seen in FIG. 2A, the primary lumen 18a may include a ramped surface 19a adjacent the opening 15a, e.g., to direct a device advanced through the primary lumen 18a out the opening 15a at a desired angle relative to the longitudinal axis 16 and/or relative to the balloon 30. For example, the ramped surface 19a and opening 15a may be configured to deploy the device at an acute angle distally relative to the longitudinal axis 16, e.g., between about ten and sixty degrees (10-60°), or between about thirty and forty five degrees (30-45°). Thus, as the device exits the opening 15a, the device may move adjacent the side wall 38 of the balloon 30 and/or into the field of view 48 of the imaging assembly 40.

Figure 3:
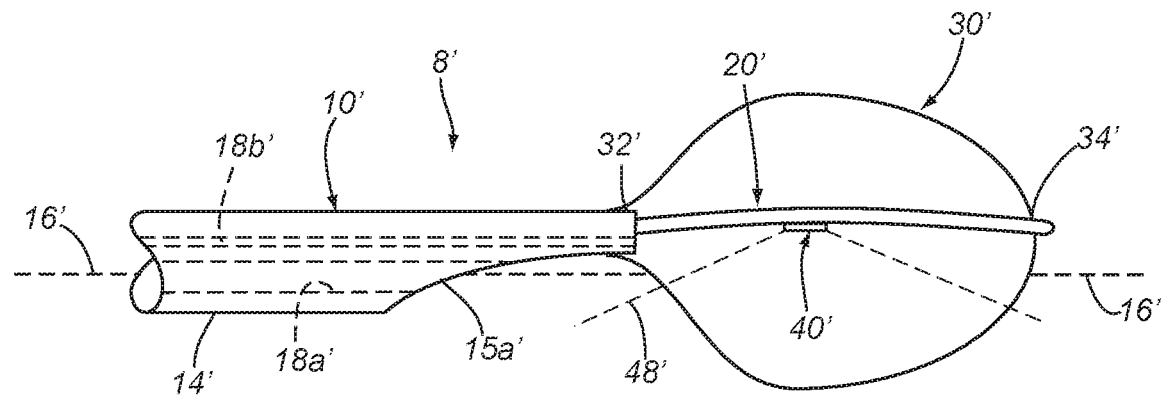
FIG. 3 is a side view of a distal portion of another exemplary embodiment of the imaging apparatus of FIG. 1 including a generally axial primary lumen opening adjacent the balloon.

Alternatively, as shown in FIG. 3, another embodiment of a distal portion 14' is shown in which an opening 15a' is provided that is aligned generally along the longitudinal axis 18' (with like components numbered similar to the apparatus 8 of FIGS. 2A and 2B but with a ' added). In this alternative, a device advanced out the opening 15a' may define a relatively small angle relative to the longitudinal axis 16,' e.g., between about zero and thirty degrees (0-30°) or between about zero and ten degrees (0-10°).

In either case, optionally, the size of the balloon 30 may be adjusted during or after deployment of the device, e.g., to adjust the angle and/or otherwise manipulate the device. For example, the device may be advanced until positioned adjacent the side wall 38, whereupon the balloon 30 may be inflated further to deflect the device out, i.e., increasing the angle relative to the longitudinal axis 16, as described further elsewhere herein. The angle of the device upon exit combined with the degree of inflation of the balloon 30 may be set to ensure that the device encounters the wall of the balloon 30 directly by being advanced from the opening 15a. In addition or alternatively, further manipulation and/or interaction with tissue may cause the device to deflect against the wall of the balloon 30.

Figure 4A:
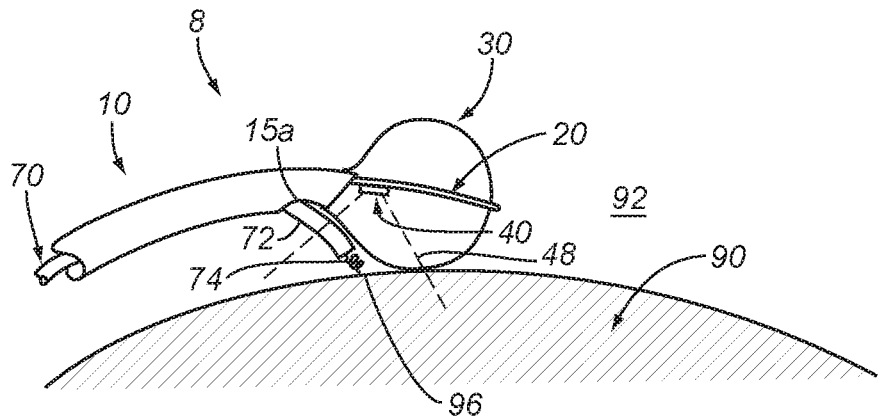
FIGS. 4A and 4B are cross-sectional views of a patient's heart showing exemplary methods for placing a cardiac lead using the apparatus of FIGS. 2A and 2B.
Figure 4B:
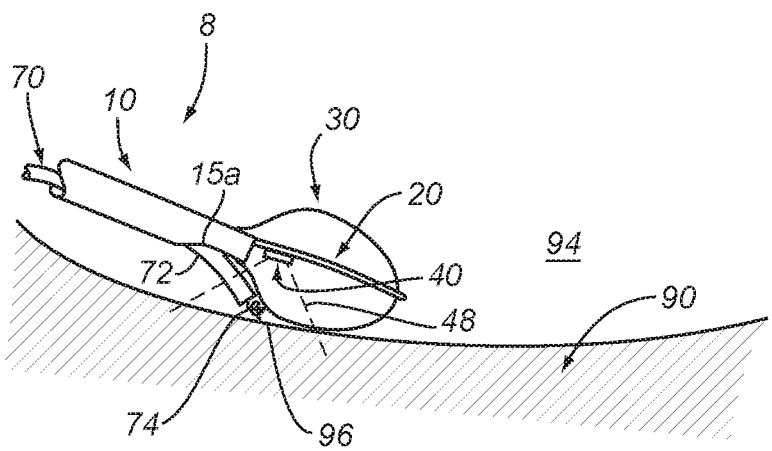

Turning to FIGS. 4A and 4B, exemplary methods are shown for performing a medical procedure within a body lumen of a patient's body using the apparatus 8 of FIGS. 2A and 2B, e.g., to deliver a cardiac lead 70 within the epicardial space 92 adjacent a patient's heart 90 (e.g., as shown in FIG. 4A) or within a chamber 94 of the heart 90 (e.g., as shown in FIG. 4B). Initially, for the procedure shown in FIG. 4A, the distal end 14 of the catheter 10 may be introduced into the patient's body, e.g., through the pericardial sac into the epicardial space 92 with the balloon 30 in the contracted condition. For example, an introducer sheath (not shown) may be introduced into the patient's chest, e.g., using minimally invasive or open surgical access, and then the distal end 14 of the catheter 10 may be inserted through the sheath until disposed adjacent the heart 90.

Once the distal end 14 is exposed within the epicardial space 92, the balloon 30 may be expanded and the catheter 10 may be manipulated to place the side wall 38 of the balloon 30 against the wall of the heart 90. For example, the catheter 10 may be rotated to orient the imaging assembly 40 towards heart 90, e.g., such that the surface of the wall is within the field of view 48 of the imaging assembly 40. The balloon 30 may provide a desired spacing between the imaging assembly 40 and the contacted tissue, which may maximize the field of view 48. The balloon 30 may also be pressed against the wall to displace fluids and/or tissues, e.g., to facilitate imaging contacting tissues.

Optionally, saline or other clear fluid may be infused using the apparatus 8 into the epicardial space 92 adjacent the balloon 30 to further clear the field of view. For example, the catheter 10 may include an infusion lumen including one or more outlets (not shown) on the distal end 14, which may be used to deliver the fluid to the outside of the balloon 30, e.g., oriented towards the side wall 38.

Figure 4C:
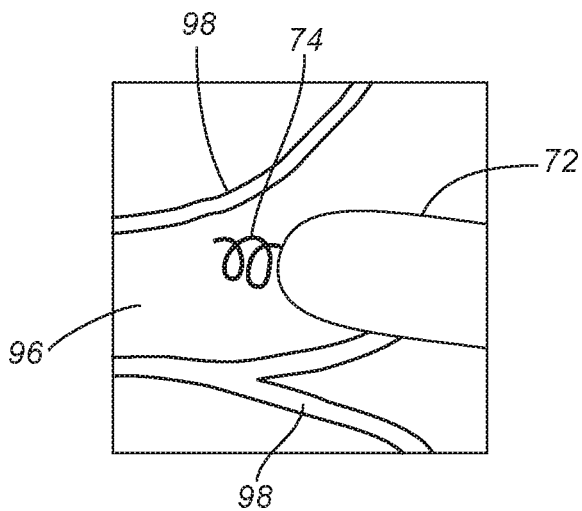
FIG. 4C is an exemplary image showing a lead deployed within a field of view of the apparatus of FIG. 4A adjacent the wall of a heart including vessels adjacent the surface.

The imaging assembly 40 may then be used to acquire images of the wall of the heart 90, e.g., as shown in FIG. 4C, while manipulating the apparatus 8. The location and/or orientation of the imaging assembly 40 on the stabilization member may be set to substantially center the field of view 48 towards the side wall 38, e.g., immediately adjacent the opening 15a to facilitate imaging a device deployed from the opening 15a. In addition, external imaging may be used, if desired in conjunction with acquiring images using the imaging assembly 40. The catheter 10 may be manipulated further as desired, e.g., to move the distal end 14 along the wall of the heart 90 until a target location 96 is identified. For example, as shown, a target location 96 may be identified in the images for placing the lead 70 while avoiding undesired anatomy such as an artery or vein 98, nerve, and/or other anatomical features. Once positioned at the target location, a distal end 72 of the lead 70 may be advanced through the primary lumen 18a and deployed from the opening 15a. Given the ramped surface 19a and side wall location of the opening 15a, the distal end 72 of the lead 70 may be deployed transversely relative to the distal portion 14.

As the distal end 72 enters the field of view 48 of the imaging assembly 40, the user may confirm the location of the tip 74, e.g., including a screw for attachment, of the distal end 72 before attaching the tip 74 into the wall of the heart 90. If desired, the apparatus 8 and/or the lead 70 may be manipulated further, e.g., to avoid the vessels 98 and/or otherwise position the tip 74 where desired. Optionally, before attaching the tip 74 in tissue, the size of the balloon 30 may be adjusted, e.g., inflated to press against the distal end 72 of the lead 70, to change the angle of the distal end 72, and/or otherwise provide refined positioning before screwing the tip 74 into the wall.

Once the tip 74 is securely screwed into the wall of the heart 90 at the target location 96, the apparatus 8 may be removed, e.g., using conventional procedures. For example, a slitter or other tool (not shown) may be provided that may be used to slit the catheter 10 from the handle 50 and proximal end 12 through the wall of the catheter 10 to the primary lumen 18 and along the length of the catheter 10 to the distal end 14. Optionally, the catheter 10 may include one or more features to enhance slittablity, e.g., including a relatively thin region extending between the proximal and distal end 12, 14. In addition or alternatively, the catheter 10 may include a relatively thick or slit-resistant region, e.g., generally opposite the relatively thin region and/or otherwise extending axially between the proximal and distal end 12, 14, which may resist the catheter 10 spiraling during slitting. Thus, in this manner, the catheter 10 may be easily slit between the proximal and distal ends 12, 14, to facilitate removing the catheter 10 from around the secured lead 70, which may remain within the patient's body. Further in addition or alternatively, the catheter 10 may include one or more features to protect connections, e.g., wires, and the like, leading to the imaging assembly 40 from being cut during slitting.

FIG. 4B shows a similar procedure for securing the tip 74 of the lead 70 in the wall of a heart 90 adjacent a chamber or other vessel 94 of the heart 90, e.g., using an endocardial approach. In this method, the distal end 14 of the apparatus 8 may be introduced into the patient's vasculature, e.g., over a guidewire and/or through an access sheath (not shown), which may be previously introduced into the vessel 94 from a percutaneous access site. Once the lead 70 is advanced through the catheter 10, the distal end 72 may be visualized using the imaging assembly 40 to position the distal end 72 before attaching the tip 74 to the wall, as described above.

Figure 5A:
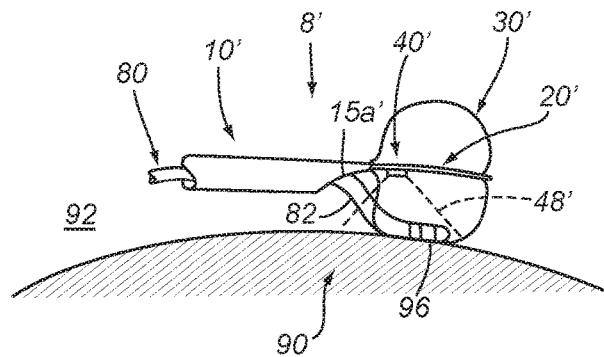
FIGS. 5A and 5B are cross-sectional views of a patient's heart showing exemplary methods for positioning an ablation probe using the apparatus of FIG. 3.
Figure 5B:
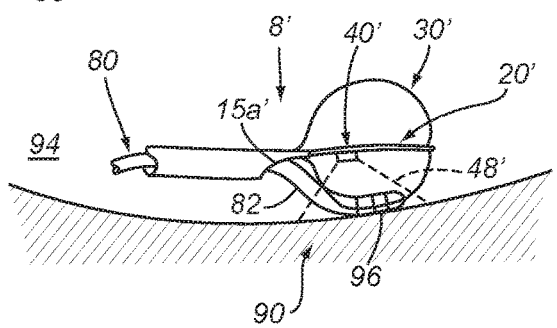

Turning to FIGS. 5A and 5B, exemplary methods are shown for performing a medical procedure within a body lumen of a patient's body using the apparatus 8' of FIG. 3, e.g., to deliver an ablation probe 80 within the epicardial space 92 adjacent a patient's heart 90 (as shown in FIG. 5A) or within a chamber 94 of the heart 90 (as shown in FIG. 5B). Generally, the apparatus 8' may be introduced into the patient's body similar to the methods described above.

For example, the distal end 14' may be introduced into the epicardial space 92 with the balloon 30' in the collapsed condition, and positioned adjacent a desired surface of the heart 90. The balloon 30' may be expanded and the side wall 38' pressed against the surface, as shown in FIG. 5A, and then the surface may be imaged using the imaging assembly 40' to identify a target location 96 for ablation.

Once the target location 96 is identified, the distal end 82 of the ablation probe 80 may be introduced through the catheter 10' and deployed from the opening 15a.' Because of the generally axial configuration of the opening 15a,' the distal end 82 may be deployed at a relatively small angle relative to the longitudinal axis 16' of the catheter 10.' Optionally, the balloon 30' may include a concave channel (not shown) adjacent the opening 15a' to guide the ablation probe 80 along the side wall 38' of the balloon 30.' In addition or alternatively, the size of the balloon 30' may be adjusted to change the angle and/or to press the distal end 82 of the ablation probe 80 against the wall of the heart 80. Similar to the exemplary image in FIG. 4C, the imaging assembly 40' may be used to avoid placing the distal end 82 of the probe 80 on vessels 98 or other undesired anatomical structures. Once properly positioned, the probe 80 may be activated to deliver energy and/or otherwise treat the tissue at the target location 96. This procedure may be repeated at one or more locations within the heart 90, as desired. Once the treatment is completed, the probe 80 and apparatus 8' may be removed from the heart 90 and the patient's body.

Figure 7A:
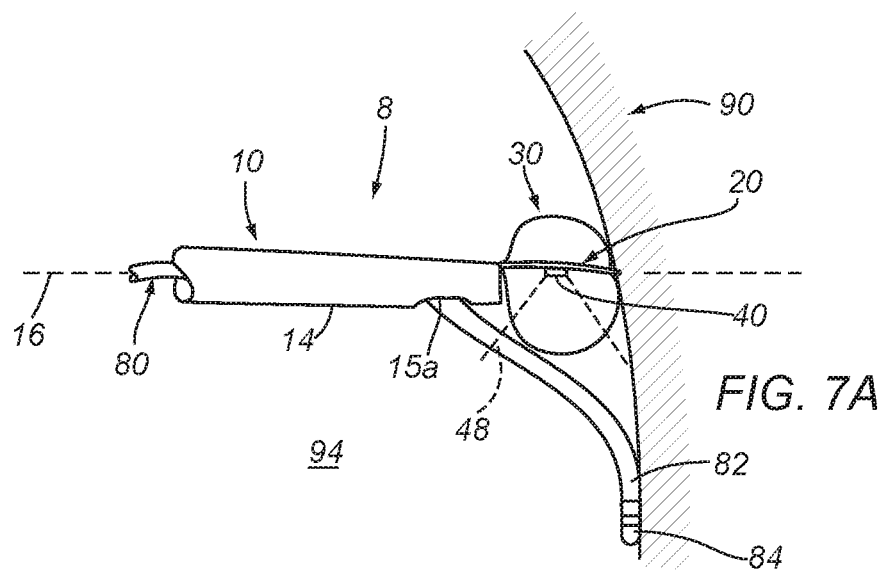
FIGS. 7A and 7B are cross-sectional views of a patient's heart showing additional exemplary methods for introducing an ablation probe and a cardiac lead, respectively.
Figure 7B:
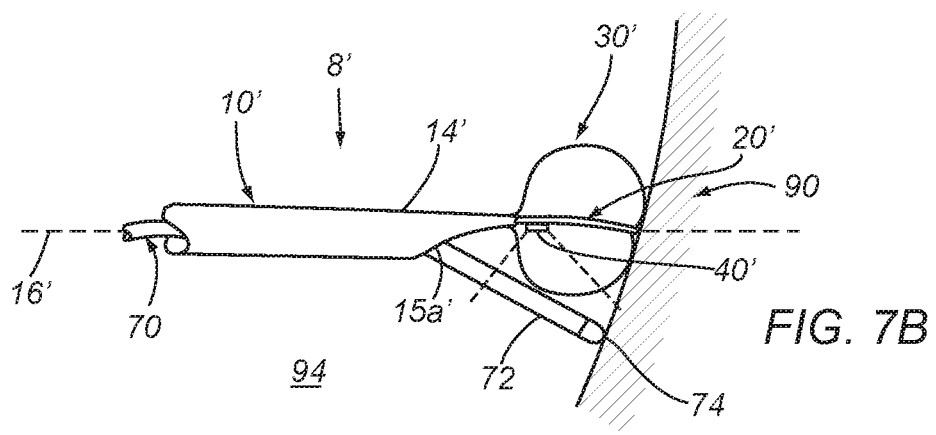

In alternative embodiments, e.g., as shown in FIGS. 7A and 7B, an apparatus 8, 8' may be used to introduce a secondary device, e.g., ablation probe 80 or lead 70, in a direction substantially orthogonal to the wall of the heart 90. For example, as shown in FIG. 7A, the apparatus 8 of FIGS. 2A and 2B may be introduced into the chamber 94 of the heart 90 with the balloon 30 collapsed. Once positioned adjacent the wall, the balloon 30 may be inflated and pressed against the wall of the heart 90, e.g., to stabilize the distal portion 14, and the imaging assembly 40 used to obtain images of the chamber 94 and wall. The ablation probe 80 may be introduced through the catheter 10 and deployed from the side opening 15a, e.g., such that the distal end 82 extends at a substantially transverse angle relative to the longitudinal axis 16. In this manner, the distal end 82 of the probe 80 may be placed along the wall of the heart 90, e.g., to position multiple electrodes or other energy delivery elements 84 against the wall of the heart to deliver energy, with the imaging assembly 40 providing visual confirmation. Similar to other embodiments, the catheter 10 and probe 80 may be manipulated as desired to position the distal end 82 at a target location and/or the size of the balloon 30 may be adjusted to modify the angle of deployment of the distal end 82 to facilitate placing the electrode(s) 84 against the wall.

In the alternative embodiment shown in FIG. 7B, the apparatus 8' of FIG. 3 is shown being used to deliver the lead 70 at a relatively low angle relative to the longitudinal axis 16' towards the wall of the heart with the imaging assembly 40' providing visual confirmation of the location of the distal end 72 of the lead 70 before attaching the tip 74 to the wall of the heart 90. Again, the balloon 30' may be inflated and/or deflated, as desired, to modify the angle of the distal end 72 while obtaining images using the imaging assembly 40' to provide more refined positioning, if desired.

Figure 6A:
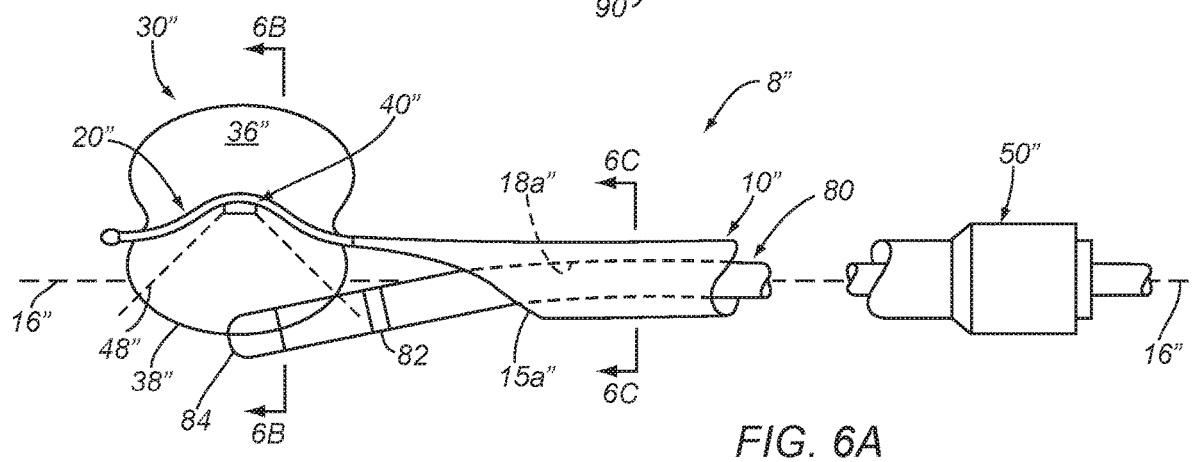
FIG. 6A is a side view of another exemplary embodiment of an imaging apparatus for delivering an ablation probe.
Figure 6B:
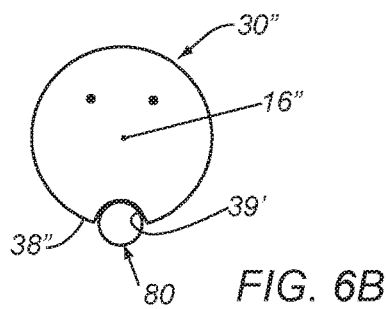
FIGS. 6B and 6C are cross-sections of the apparatus of FIG. 6A taken along slices 6B-6B and 6C-6C, respectively.
Figure 6C:
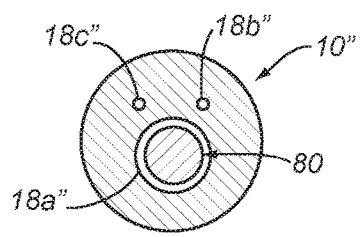

Turning to FIG. 6A, another embodiment of an apparatus 8" for delivering an ablation probe 80 is shown that includes a catheter 10" having a generally on-axis opening 15a" communicating with the primary lumen 18a," similar to the embodiment shown in FIG. 3. In this embodiment, the stabilization member 20" may have a curvilinear shape in which the imaging assembly 40" is carried on an intermediate region that is spaced further from the longitudinal axis 16" than the ends of the stabilization member 20." This configuration may maximize the field of view 48" of the imaging assembly 40" to facilitate viewing the secondary device (e.g., ablation probe 80) introduced through the primary lumen 18a" and deployed from the opening 15a." More generally, the stabilization member 20" may be shaped or otherwise configured to position the imaging assembly 40" at a predetermined location, e.g., to maximize size and/or position of the field of view 48" and/or to avoid passing of the stabilization member 20" through the field of view 48."

In addition, the balloon 30" may have an everted shape and/or may have an asymmetrical shape, e.g., defining a recess or channel 39" aligned with the opening 15a," e.g., such that the probe 80 deployed from the opening 15a" may enter the channel 39" and/or otherwise slide along the side wall 38" of the balloon 30," which may enhance imaging the probe 80. In addition or alternatively, the balloon 30" may be substantially compliant such that the side wall 38" wraps partially around the probe 80, e.g., when the distal end 82 of the probe 80 is pressed between the side wall 38" and the wall of a body lumen (not shown). Optionally, cooling fluid may be delivered into the interior 36" of the balloon 30," e.g., to prevent overheating of the distal end 82 of the probe 80, e.g., when energy is delivered to ablate tissue via RF electrodes or other energy delivery elements 84 on the distal end 82 and/or to the immediate area around the probe 80, i.e., outside of the balloon 30."

Turning to FIGS. 8A-8D, still another embodiment of an imaging apparatus 108 is shown that includes a catheter 110 including a proximal end 112 with a handle 150, a distal end 114 sized for introduction into a patient's body, and one or more lumens extending between the proximal and distal ends 112, 114, e.g., a primary lumen 118a, similar to other embodiments herein. Unlike the previous embodiments, the apparatus 108 includes a pair of balloons 130 carried by separate stabilization members 120, and an imaging assembly 140 carried by a dome element 142 coupled to the balloons 130.

In particular, each stabilization member 120 includes a first end 122 attached to the distal end 114 of the catheter 110 and a second end 124 coupled together at the distal tip 125. The stabilization members 120 may be biased to bow outwardly from one another at an intermediate region while lying substantially within a single plane. For example, the stabilization members 120 may be compressible towards one another, e.g., to reduce a profile of the apparatus 108 for introduction into a patient's body, yet biased to return to the bowed shape once deployed within a body lumen. The stabilization members 120 may also be sufficiently flexible to accommodate bending during introduction, e.g., through tortuous anatomy between an entry site and the target body lumen, similar to other embodiments herein.

Figure 8A:
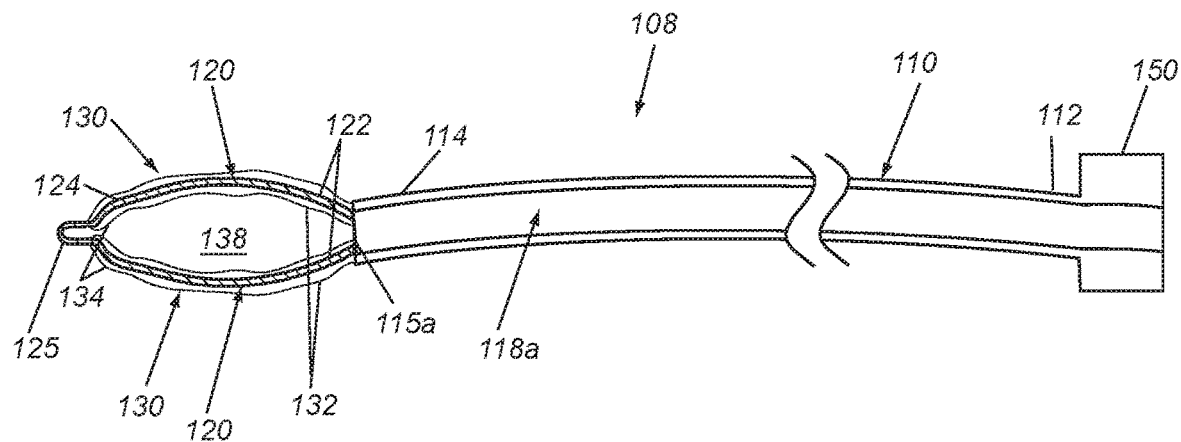
FIGS. 8A and 8B are top and side views, respectively, of yet another embodiment of an imaging apparatus including a pair of balloons supporting an imaging assembly.
Figure 8B:
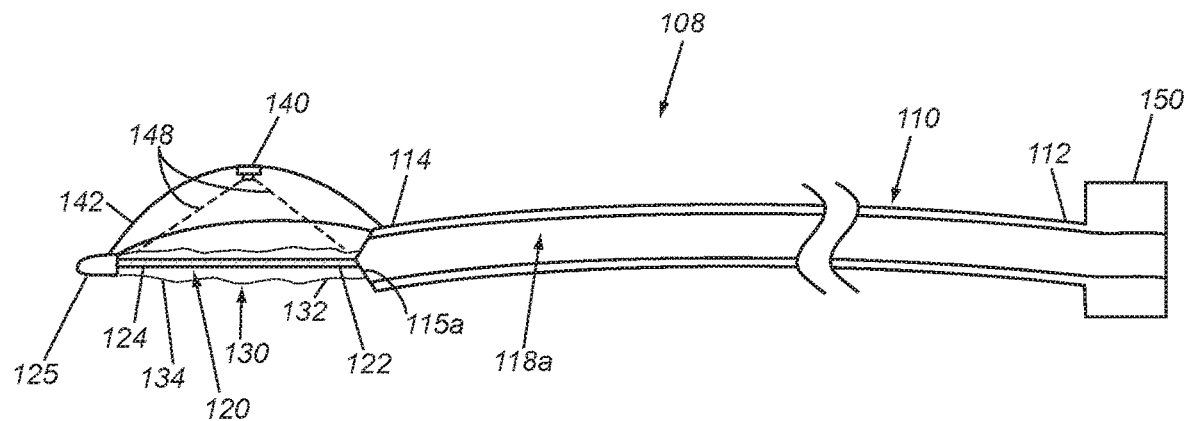
Figure 8C:
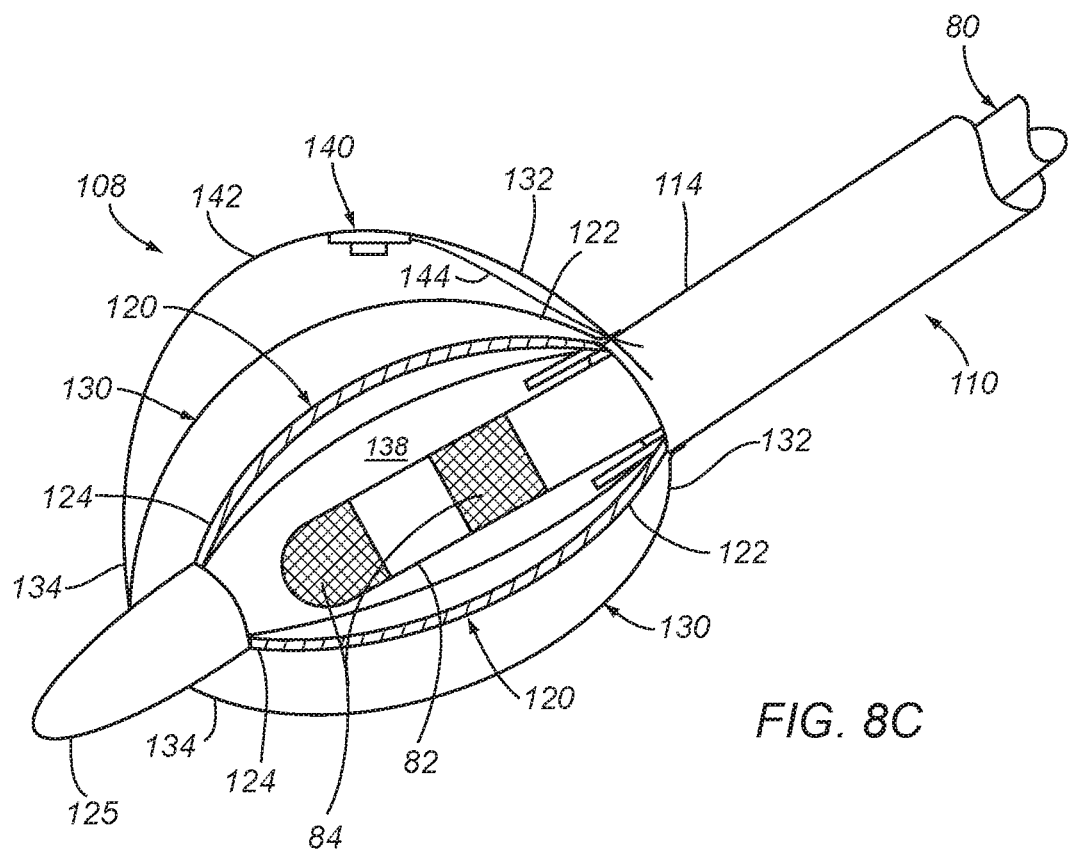
FIG. 8C is a bottom view detail of a distal portion of the apparatus of FIGS. 8A and 8B, showing an ablation probe being deployed from the apparatus between the balloons.

Each balloon 130 may include a first end 132 coupled to the first end 122 of the respective stabilization member 120 and/or to the distal end 114 of the catheter 110, and a second end 134 coupled to the second end 124 of the respective stabilization member 120. In this configuration, when inflation media is delivered into the interiors of the balloons 130, the balloons may expand in a curved shape corresponding to the bowed shape of the stabilization members 120, thereby providing an open area 138 between the balloons 130. As can be seen in FIG. 8C, when ablation probe 80 (or other secondary device) is delivered through the primary lumen 118a and out the opening 115a, the distal end 82 may be disposed within the open area 138, e.g., between and/or slightly below the expanded balloons 130. In this way, multiple balloons may be utilized to create an imageable working space within the body where an ablation probe 80 or other device may be delivered and utilized under direct visualization.

Figure 8D:
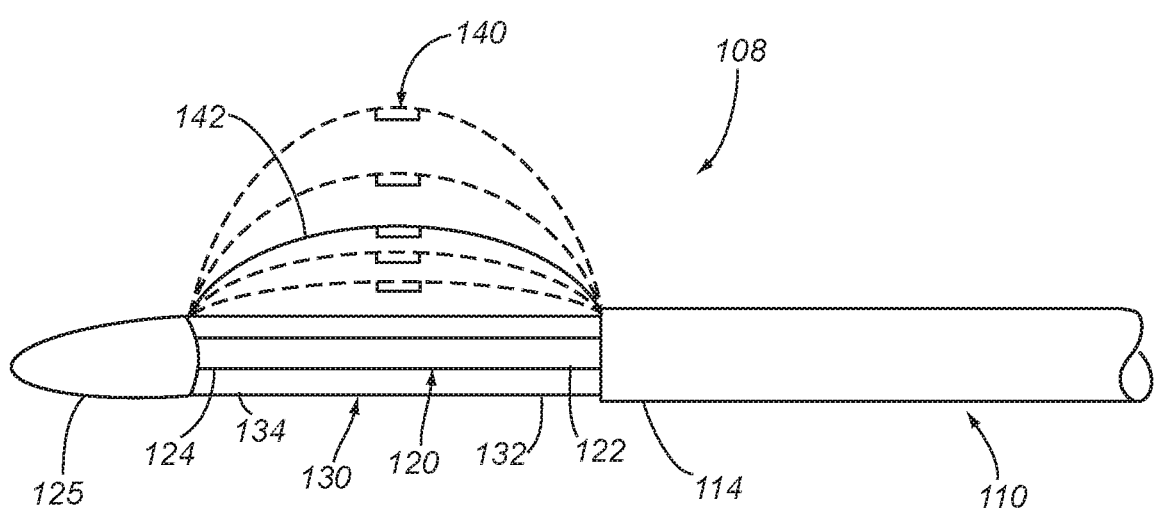
FIG. 8D is a side view detail of the distal portion of the apparatus of FIGS. 8A and 8B, showing the imaging assembly being positioned at different heights depending on the extent of inflation of the balloons.

The imaging assembly 140 may be carried on the dome element 142, e.g., on an inner surface thereof between the stabilization members 120 and oriented towards the open area 139, e.g., such that the field of view 148 of the imaging assembly 140 is substantially centered on the open area 139. One or more cables, fibers, and the like 144 may extend from the imaging assembly 140 along the dome element 142 into corresponding lumen(s) (not shown) in the distal portion 114. When the balloons 130 are inflated, the dome element 142 may be lifted away from the open area 138, e.g., as shown in FIG. 8D, thereby increasing the size of the field of view 148. With the stabilization members 120 bowed outwardly away from one another at the intermediate region, the stabilization members 120 may be disposed at the outer periphery of the field of view 148, e.g., thereby minimizing interference with the open area 138 between the balloons 130.

When the ablation probe 80 is introduced into the apparatus 108 and the distal end 82 deployed from the opening 115a into the open area 138, the distal end 82 may be imaged using the imaging assembly 140. Thus, similar to other embodiments herein, the imaging assembly 140 may be used to facilitate positioning the distal end 82 of the probe 80 relative to a target location on the wall of the heart or other body lumen (not shown). Optionally, the balloons 130 may be inflated further, e.g., to press the distal end 82 against the wall and/or otherwise, facilitate positioning the distal end 82 and/or enhancing contact with tissue before delivering energy, similar to other embodiments herein.

Figure 9A:
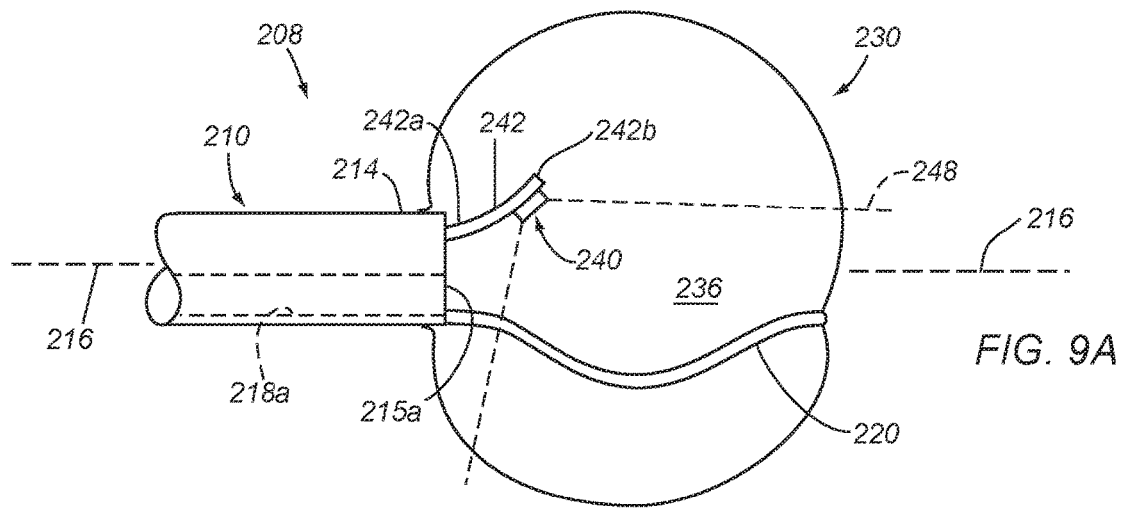
FIGS. 9A and 9B are side views of a distal portion of still another embodiment of an imaging apparatus including an asymmetrical balloon carried by a divided stabilization member being used to deliver an ablation probe.
Figure 9B:
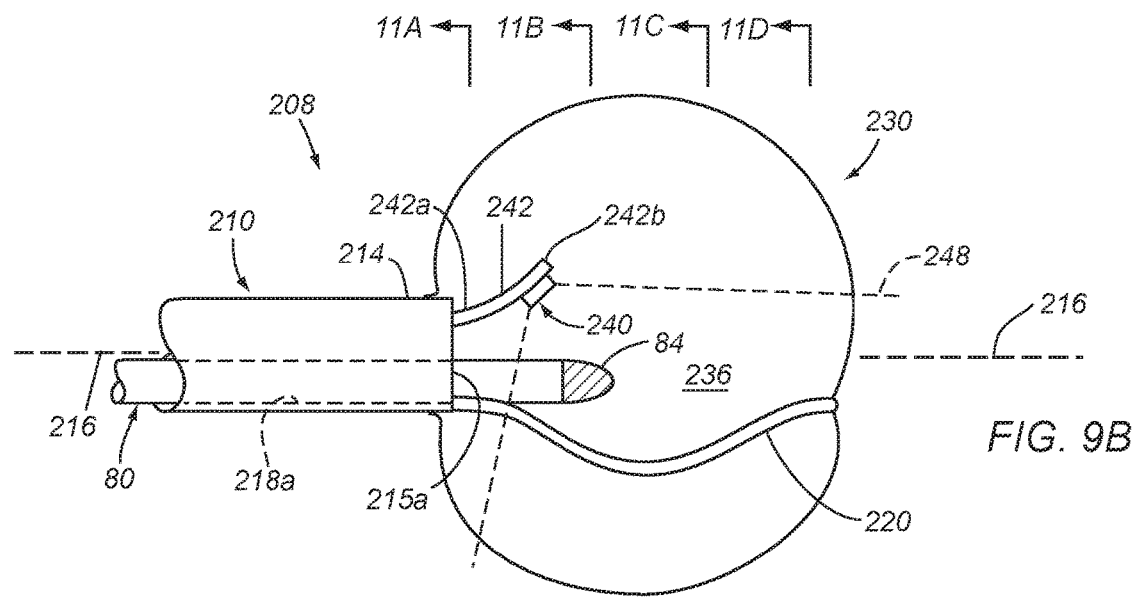
Figures 11A, 11B, 11C, 11D:
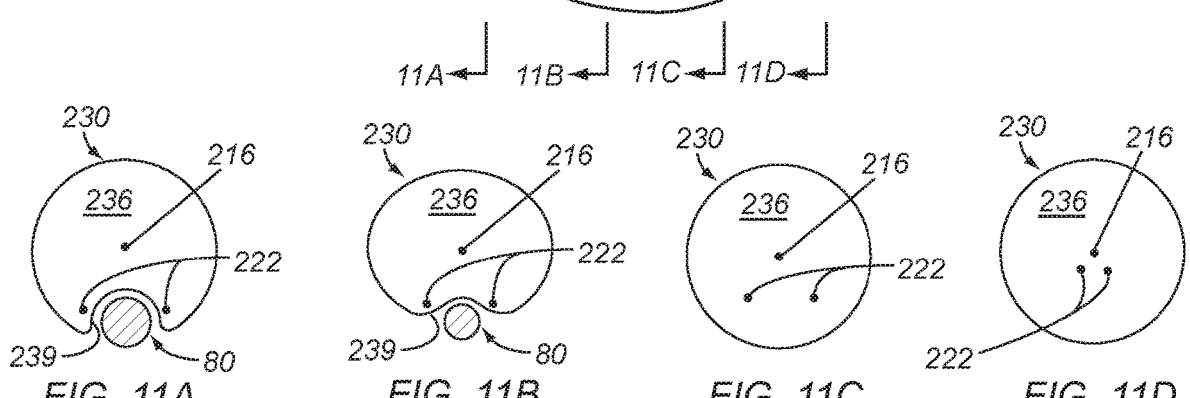
FIGS. 11A-11D are cross-sections of the apparatus of FIG. 9B taken along slices 11A-11A to 11D-11D, respectively.

Turning to FIGS. 9A and 9B, yet another embodiment of an imaging apparatus 208 is shown that includes a catheter 210 including a proximal end (not shown), a distal end 214 sized for introduction into a patient's body, and one or more lumens extending between the proximal and distal ends 214, e.g., a primary lumen 218a, similar to other embodiments herein. In addition, the apparatus 208 includes a stabilization member 220 that includes a pair of arms 222 extending between the distal end 214 and a distal tip 225 of the apparatus 208 and carrying a balloon 230, also generally similar to previous embodiments.

Unlike the previous embodiments, the apparatus 208 includes an imaging assembly 240 on a separate support structure 242 coupled to the distal end 214 of the catheter 210. The support structure 242 may be an arm including a first end 242a fixedly attached to the distal end 214 and a second free end 242b biased to define an acute angle relative to the longitudinal axis 216 of the catheter 210.

The imaging assembly 240 may be mounted on the second end 242b of the support structure such that the field of view 248 of the imaging assembly 240 extends transversely relative to the longitudinal axis 260. For example, the field of view 248 may have a central axis that intersects the longitudinal axis 260 to define an acute angle, e.g., similar to other imaging assemblies described elsewhere herein.

Optionally, the support structure 242 may be actuatable to change the orientation of the field of view 248 of the imaging assembly 240. For example, a cable or other actuator element (not shown) may be coupled to the free end 242b of the arm 242, which may be actuated to increase or decrease the angle the field of view 248 defines relative to the longitudinal axis 216. For example, the field of view 248 may be directed such that it is substantially perpendicular to the longitudinal axis 216, may be directed such that the field of view 248 defines an acute angle in a proximal direction, e.g., such that the field of view 248 is oriented in a partial backward looking condition, and/or may be directed such that the field of view 248 defines an acute angle in a distal direction, e.g., such that the field of view 248 is oriented in a partial forward looking condition. In addition or alternatively, the support structure 242 may be actuatable laterally, e.g., to allow the field of view 248 to be directed left or right of the longitudinal axis 216. In yet a further alternative, the imaging assembly 240 (or any of the other embodiments herein) may be fixed in forward, backward, or substantially perpendicular orientations.

Thus, in this embodiment, the imaging assembly 240 may optionally be movable in multiple directions, i.e., have multiple degrees of freedom of movement to direct the field of view 248 in desired directions. Optionally, imaging assemblies in other embodiments herein may be movable, e.g., relative to the stabilization member and/or other support structure to direct the field of view in one or more directions, if desired. In another alternative, the stabilization members and/or other support structures may be actuatable, e.g., using one or more pull wires or other steering elements to change the direction of the field of view of the imaging assembly.

Figure 10A:
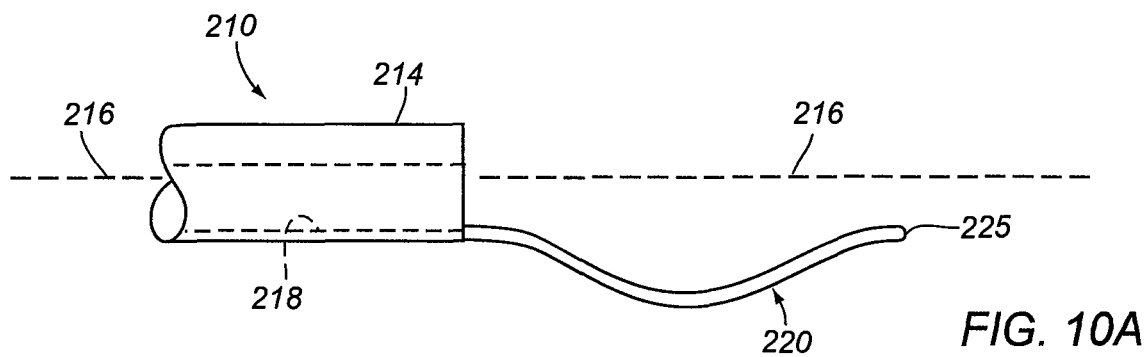
FIGS. 10A and 10B are side and top views, respectively, of the apparatus of FIGS. 9A and 9B, showing the stabilization member attached to the catheter before attachment of the balloon.
Figure 10B:
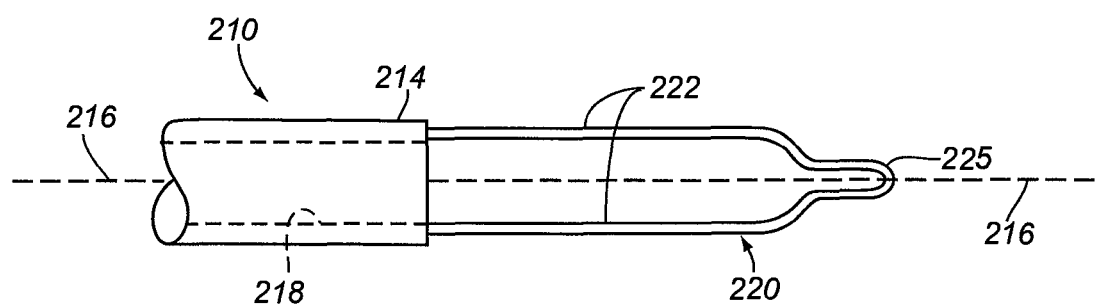
Figure 9C:
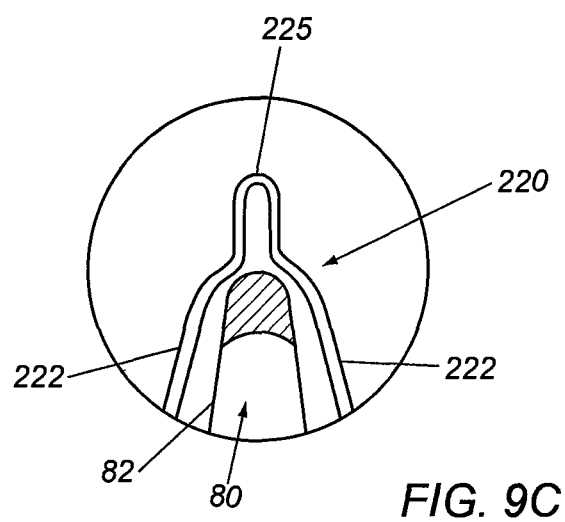
FIG. 9C is an exemplary image acquired using the apparatus of FIGS. 9A and 9B, showing the ablation probe and stabilization member within the field of view.

Returning to FIGS. 9A-9C, in this embodiment, the arms 222 of the stabilization member 220 may lie within the field of view 248, e.g., as shown in FIG. 9C. As best seen in FIGS. 10A and 10B, the stabilization member 220 may have a curvilinear shape, e.g., such that the arms 222 extend substantially parallel to one another from the distal end 214 to the distal tip 225, as shown in FIG. 10B, yet both curve away from the longitudinal axis 216 at an intermediate region between the distal end 214 and the distal tip 225, as shown in FIG. 10A.

The arms 222 of the stabilization member 220 may be coupled to the balloon 230 to provide an asymmetrical shape for the balloon 230 when expanded. For example, as can be seen in FIGS. 11A-11D, the arms 222 may support the balloon 230 to create a channel or concave recess 239 immediately adjacent the outlet 215a of the primary lumen 218a. In this manner, when the balloon 230 is inflated the channel 239 may provide a transition or guide from the outlet 215a, e.g., to guide the probe 80 during deployment from the distal portion 214 along the outer surface of the balloon 230, e.g., into the field of view 248 of the imaging assembly 240. Optionally, similar to other embodiments, during or after deployment of the probe 80, the balloon 230 may be further inflated, deflated, and/or otherwise adjusted to facilitate positioning and/or stabilizing the distal end 82 of the probe 80, and/or press the distal end 82 against target tissue, e.g., to perform an ablation of other procedure.

Turning to FIGS. 12A and 12B, another embodiment of an apparatus 308 is shown that includes a catheter 310 carrying a balloon 330 and an imaging assembly 340 on its distal portion 314, generally similar to other embodiments. In the embodiment shown, the imaging assembly 340 may be mounted to an inner surface of the balloon 340, e.g., thereby providing a field of view across the longitudinal axis 316 and out the opposite side wall of the balloon 330. Alternatively, the imaging assembly 340 may be attached to a surface of the balloon 330 using a tether or other element (not shown). In addition or alternatively, the imaging assembly 340 may be located outside the balloon 330 and oriented to provide a field of view through both side walls of the balloon 330 to an opposite side, e.g., to view a device deployed from the catheter 310. In still another alternative, the imaging elements and the light sources of the imaging assembly 340 may be located at different locations (as may also be the case with other embodiments herein). For example, the light sources may be placed at multiple locations separate and/or spaced from the imaging element(s) (not shown) to provide a desired lighting configuration for the images obtained using the imaging assembly 340.

A plurality of stabilization or redirection elements 320 are provided that support the balloon 330, e.g., to direct the balloon 330 to an asymmetrical shape when expanded from a collapsed condition (shown in FIGS. 12A and 12C) and an expanded condition (shown in FIGS. 12B, 12D, and 12E). The stabilization elements 320 generally extend from the distal portion 314 to a distal tip 325 of the apparatus 308 and may be biased to predetermined shapes yet sufficiently flexible to accommodate introduction into a patient's body, similar to previous embodiments.

As best seen in FIGS. 12C and 12D, the stabilization elements 320 include a first elongate member 320a, which extends along an outer surface of the balloon 330, and a pair of second elongate members 320b, which extend within the interior 336 of the balloon 330, generally along the longitudinal axis 316. In one embodiment, the first elongate member 320a may be substantially straight and may be aligned along the longitudinal axis 316, while the second elongate members 320b may be offset from the longitudinal axis 316, e.g., within the same plane.

In this manner, when the balloon 330 is inflated, the inner surface of the balloon 330 adjacent the second elongate members 320b may be constrained relative to the outer surface of the balloon 330 adjacent the first elongate member 320a, thereby causing the balloon 330 to expand asymmetrically, e.g., to define a channel or recess 339 between the elongate members 320 along the outer surface of the balloon 330. Similar to other embodiments, the channel 339 may be aligned with an opening (not shown) of a primary lumen 318a of the catheter 310. Thus, when a device, e.g., distal end 82 of ablation probe 80, is introduced through the primary lumen 318a and deployed from the opening, the distal end 82 may slide along the channel 339, e.g., to guide the distal end 82 along the balloon 330. Optionally, the size of the balloon 330 may be adjusted to change the angle of deployment of the distal end 82 and/or press the distal end 82 between the balloon 330 and an adjacent tissue structure, also similar to other embodiments herein. In this manner, the ablation probe 80 may be introduced under direct visualization using the imaging assembly 340 to perform an ablation procedure.

In an alternative embodiment, shown in FIGS. 13A and 13B, the balloon 330' may be constrained by stabilization or redirection elements 320' to provide a different asymmetrical shape. In this embodiment, a first elongate member 320a' is disposed within the interior 336' of the balloon 330' while a pair of second elongate members 320b' are disposed outside the balloon 330.' When the balloon 330' is inflated from the collapsed condition, shown in FIG. 13A, to the expanded condition, shown in FIG. 13B, the elongate members 320' may constrain the balloon 330' to adopt a different asymmetrical shape, e.g., including a pair of channels or recesses 339.' The balloon 330' may be incorporated into any of the embodiments herein, where it is desired to provide the asymmetrical shape and/or channels 339' and used similar to other embodiments herein.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for imaging tissue structures of a patient's heart, comprising:
   introducing a distal end of a tubular member into an epicardial space adjacent the patient's heart;
   expanding a balloon on the distal end within the epicardial space;
   acquiring one or more images of an area adjacent a side wall of the balloon using an imaging assembly permanently mounted on the tubular member distal end within an interior of the balloon to identify a target location;
   deploying a device from an opening in the tubular member distal end proximal to the balloon to a location outside and lateral to the balloon; and
   positioning the device adjacent the target location while imaging using the imaging assembly,
   wherein the imaging assembly is oriented on the tubular member to acquire images such that a center axis of a field of view of the imaging assembly is oriented transversely relative to a longitudinal axis of the tubular member such that the device is within a field of view of the imaging assembly when deployed from the opening.

2. The method of claim 1, further comprising treating the target location using the device.

3. The method of claim 2, wherein the device is positioned against the epicardium of the patient's heart while imaging using the imaging assembly to avoid placing the device adjacent undesired anatomical structures.

4. The method of claim 3, wherein the device comprises an ablation probe, wherein treating the target location comprises activating the ablation probe to deliver energy to the target location, and wherein the ablation probe is positioned to avoid placing the probe adjacent vessels within the wall of the patient's heart before activating the ablation probe.

5. The method of claim 1, wherein the device is deployed from the opening at an angle relative to a longitudinal axis of the tubular member that is between about zero and thirty degrees (0-30°).

6. The method of claim 5, wherein positioning the device comprises increasing a size of the balloon to deflect the device outwardly relative to the longitudinal axis.

7. The method of claim 1, wherein the device is deployed from the opening transversely at an angle relative to a longitudinal axis of the tubular member.

8. The method of claim 7, wherein positioning the device comprises changing a size of the balloon to change the angle of the device relative to the longitudinal axis.

9. The method of claim 1, further comprising a stabilization member attached to and extending from the tubular member distal end to a distal tip, and wherein the balloon includes a first end attached to the tubular member distal end and a second end attached to the stabilization member adjacent the distal tip.

10. A method for imaging tissue structures of a patient's heart, comprising:
    introducing a distal end of a tubular member into an epicardial space adjacent the patient's heart;
    expanding a balloon on the distal end within the body lumen;
    acquiring one or more images of an area adjacent a side wall of the balloon using an imaging assembly permanently mounted on the tubular member distal end to identify a target location;
    deploying a device from an opening in the tubular member distal end proximal to the balloon to a location outside and lateral to the balloon; and
    positioning the device against a wall of the heart adjacent the target location while imaging using the imaging assembly,
    wherein the imaging assembly is oriented on the tubular member to acquire images such that a center axis of a field of view of the imaging assembly is oriented transversely relative to a longitudinal axis of the tubular member such that the device is within a field of view of the imaging assembly when deployed from the opening.

11. The method of claim 10, wherein the device comprises a lead, and wherein positioning the device comprises confirming a location of a tip 74 of the lead before attaching the tip into the wall of the heart.

12. The method of claim 11, further comprising screwing the tip of the lead into the wall of the heart.

13. The method of claim 10, wherein the device comprises an ablation probe, the method further comprising activating the ablation probe to deliver energy to the target location.

14. The method of claim 11, wherein the ablation probe is positioned to avoid placing the probe adjacent vessels within the wall of the patient's heart before activating the ablation probe.

15. A method for imaging tissue structures within a patient's heart, comprising:
    introducing a distal end of a tubular member into an epicardial space of the patient's heart, the tubular member comprising a stabilization member permanently attached to and extending from the tubular member distal end to a distal tip;
    expanding a substantially transparent balloon on the distal end within the epicardial space such that the balloon surrounds an imaging assembly mounted on an intermediate location of the stabilization member such that a center axis of a field of view of the imaging assembly is oriented transversely relative to a longitudinal axis of the tubular member;
    acquiring one or more images of an area adjacent a side wall of the balloon using the imaging assembly to identify a target location;
    deploying a device from an opening in the tubular member distal end proximal to the balloon to a location outside and lateral to the balloon; and
    positioning the device adjacent the target location while imaging using the imaging assembly.

16. The method of claim 15, wherein the imaging assembly is oriented to acquire images transversely such that the device is within a field of view of the imaging assembly when deployed from the opening.

17. The method of claim 15, wherein positioning the device comprises positioning the device against a wall of the heart adjacent the target location while imaging using the imaging assembly.

18. The method of claim 1, wherein the balloon is expanded to displace blood or other fluid from between the balloon and the epicardium to facilitate imaging through the balloon.

19. The method of claim 1, further comprising infusing clear fluid into the epicardial space adjacent the balloon to clear the field of view of the imaging element.

20. The method of claim 13, further comprising adjusting a size of the balloon to change an angle of the ablation probe or press the ablation probe against the epicardium of the heart.

* * * * *